United States Patent
Zegers

Patent Number: 5,885,563
Date of Patent: Mar. 23, 1999

[54] SHAVING LIQUID

[75] Inventor: Cornelis P.G.M. Zegers, Drachten, Netherlands

[73] Assignee: U.S. Philips Corporation, New York, N.Y.

[21] Appl. No.: 935,588

[22] Filed: Sep. 23, 1997

[30] Foreign Application Priority Data

Apr. 24, 1997 [EP] European Pat. Off. .............. 97201225

[51] Int. Cl.⁶ ...................................................... A61K 7/15
[52] U.S. Cl. ........................... 424/73; 424/401; 514/937; 514/975; 514/762
[58] Field of Search ....................... 424/73, 401; 514/762

[56] References Cited

U.S. PATENT DOCUMENTS

| | | | |
|---|---|---|---|
| 5,576,064 | 11/1996 | Fructus | 424/401 |
| 5,688,752 | 11/1997 | Turner | 425/450 |

FOREIGN PATENT DOCUMENTS

| | | |
|---|---|---|
| 0323798 A2 | 7/1989 | European Pat. Off. . |
| 0422862 A2 | 4/1991 | European Pat. Off. . |
| 2663847 | 1/1992 | France . |
| 01-203036 | 8/1989 | Japan . |

*Primary Examiner*—Thurman K. Page
*Assistant Examiner*—James M. Spear
*Attorney, Agent, or Firm*—Ernestine C. Bartlett

[57] ABSTRACT

A shaving emulsion for an electric shaver is provided, which comprises water, n-decyl glucoside as a surfactant, and 2,2,4,4,6,8,8-heptamethylnonane (isohexadecane) as a lubricant. The shaving emulsion has excellent shaving properties, and is compatible with lacquer, printings and plastic, electrical, rubber and metal parts of the electric shaver. The mixture ensures that the shaving head can be very effectively rinsed and cleaned with water, so that an electric shaver which comprises a container in the form of a flexible plastic pouch (1) filled with such a shaving emulsion, is hygienic in use.

5 Claims, 1 Drawing Sheet

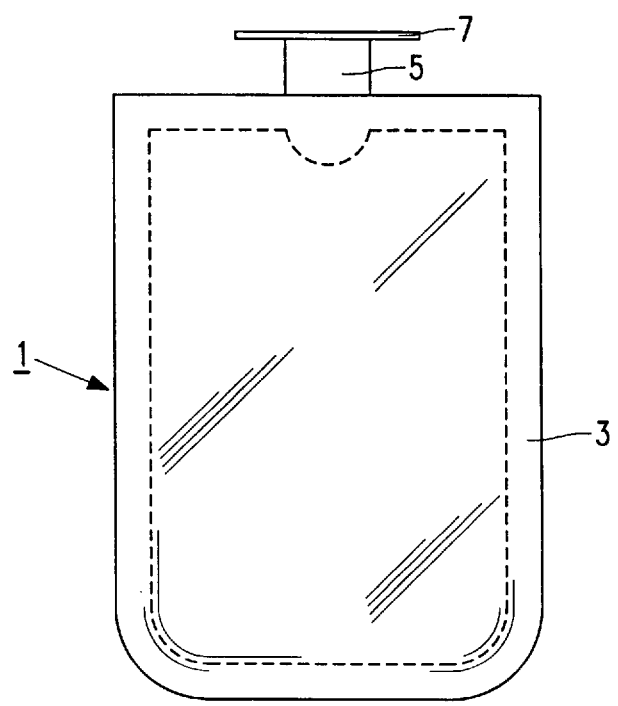

SHAVING LIQUID

FIELD OF THE INVENTION

The invention relates to a shaving liquid for a shaving system, which comprises water as a main component, usual additives and a surfactant. The invention also relates to a container filled with such a shaving liquid for a shaving system. Shaving systems include electric shavers, manual razors and depilating devices.

BACKGROUND OF THE INVENTION

Such a shaving liquid is applied to the surface of the skin prior to and during shaving beards or unwanted hairs with a(n) (electric) shaver for the purpose of conditioning the skin so that it feels soft, smooth and moisturized and to improve the shaving effect.

In the European patent application EP-A-323798 aqueous skin formulations, such as a preshave, are disclosed, which prevent or reduce the deposition of shaving cream or shaving soap on the skin. The disclosed formulation comprises a polyethylene glycol ether as a nonionic surfactant.

The non-prepublished European patent application EP 96202400.6 (PHN 15936) filed by Applicants describes a shaving system comprising an electric shaver and a container. The shaver comprises a shaver head, and a hair chamber adapted to accommodate the container. The container comprises a reservoir filled with a shaving substance, a discharge channel, and feeder means, such as a diaphragm pump, for conveying the shaving substance from the reservoir to the discharge channel. The discharge channel is coupled to a discharge opening in the shaving head for dispensing the shaving substance to the skin prior to and during shaving. A press-button at the exterior of the shaver is coupled to an actuator for actuating the diaphragm pump.

A disadvantage of the known skin formulation is that the lubrication properties between the shaver head and the skin surface are poor due to the absence of suitable lubricants. The above-mentioned EP-A-323798 discloses the use of silicones (polysiloxanes), however, they have a detrimental effect on the electrical contacts within the electric shaver due to the formation of silicon oxides. Another disadvantage is that a mixture of shaved-off hairs and the shaving substance, which is formed in the hair chamber during shaving, cannot be easily rinsed off or out with water. As a result, the hair chamber and the shaver head are difficult to clean, so that these parts become soiled with residues of said mixture. These residues readily give rise to the growth of bacteria, so that there is a risk of infection of the user of the shaving system.

SUMMARY OF THE INVENTION

It is an object of the invention to provide a shaving liquid, which can easily be rinsed from the shaving system with water, and is therefore hygienic in use. Moreover, it is an object to provide a shaving liquid which has excellent shaving characteristics and excellent lubrication properties between the shaver head and the skin surface. In particular, the shaving liquid according to the invention must be free of polysiloxanes and must be compatible with the plastic, metal and electrical parts of an electric shaver, and with rubbers, printings and lacquers, i.e. the shaving liquid may not attack or corrode parts of the shaving system.

Another object of the invention is to provide a container comprising such a shaving liquid for use in a shaving system as described above.

These objects are achieved by a shaving liquid as specified in the opening paragraph, characterized in that the liquid is an emulsion of at least a liquid hydrocarbon in water and that the surfactant is n-decyl glucoside. The shaving liquid according to the invention is a milky-white emulsion of one or more hydrocarbons in water. This emulsion can be easily rinsed off from the shaver head and the hair chamber.

The main component of the shaving liquid is (demineralized) water in an amount of about 60 to 80% by weight.

Preferably, the amount of n-decyl glucoside is 2 to 10% by weight. Below 2% the rinsing properties with water are poor, whereas above 10% no further improvement is achieved.

The hydrocarbon used may be a straight-chain or branched liquid hydrocarbon having about 10 to 30 carbon atoms. Particularly good results are obtained with 2,2,4,4,6,8,8-heptamethylnonane (or isohexadecane). Another useful hydrocarbon is squalane (2,6,10,15,19,23-hexamethyltetracosane)($C_{30}H_{62}$). These hydrocarbons act as a lubricant (emollient), and are present between the skin surface and the shaver head during shaving.

Preferably, the emulsion comprises 10 to 25% by weight 2,2,4,4,6,8,8-heptamethylnonane ($C_{16}H_{34}$). Below 10% the lubricating properties are poor. Above 25% the hydrocarbon cannot be emulsified anymore.

In a preferential embodiment, the shaving liquid comprises about 5% by weight glycerine (1,2,3-propanetriol) as a moisturizer.

The shaving liquid may also optionally comprise additives, such as anti-irritants, preservatives, thickening agents, skin-soothing agents, fragrances (perfumes), etc.

Examples of anti-irritants which are compatible with the shaving liquid according to the invention are allantoin ([2,5-dioxo-4-imidazolidinyl]urea) and D-panthenol (2,4-dihydroxy-N-[3-hydroxypropyl]-3,2-dimethylbutanamide).

A suitable preservative is 2-bromo-2-nitropropane-1,3-diol (trademark Myacide BT).

Suitable thickening agents are polyacrylic acid resins, such as Carbopol Ultrez 10, supplied by BFGoodrich.

Suitable skin-soothing agents are menthol and camphor.

Preferably, the shaving liquid also comprises a compound which adapts the pH to that of the human skin (pH=5.5–6.0). A suitable compound, which does not irritate the skin, is tetrahydropropyl ethylenediamine (trademark Neutrol TE).

The above mentioned additives are present in a small amount ranging from about 0.02 to 1% by weight.

For dispensing the shaving liquid to the surface of the skin during shaving, the housing of the (electric) shaver accommodates a container filled with the shaving liquid according to the invention. For this purpose, the shaving head of the shaver is provided with one or more discharge openings which correspond with a discharge spout of the container. Preferably, the container is a flexible reservoir made in the form of a thin-walled plastic pouch. The plastic is e.g. polyethene or polyethyleneterephtalate. To avoid sweating through of the shaving liquid, the plastic is coated with a thin metal layer, e.g aluminum. Such a flexible pouch can be manufactured easily and cheaply, and its shape readily adapts to the shape of the housing on the inside of the shaver. Moreover, by making the reservoir flexible, it is achieved that a part of the shaving liquid can be pumped out of the reservoir without entry of air into the reservoir. Air in the reservoir is undesirable, because it may cause degrading of the shaving liquid and it may lead to air finding its way into the discharge spout, so that the discharge of the shaving liquid becomes irregular or even stops completely.

BRIEF DESCRIPTION OF THE DRAWINGS

The invention will be elucidated with reference to the embodiment described hereinafter and the accompanying schematic drawing, in which FIG. 1 is a plan view of a container for a shaving system.

DETAILED DESCRIPTION OF THE PREFERRED EMBODIMENTS

Exemplary embodiment 1

A shaving liquid is prepared according to the formulation indicated in the Table.

TABLE

| Compound | | amount % |
|---|---|---|
| chemical name | trade or trivial name | by weight |
| n-decyl glucoside | Oramix NS 10 | 3.0 |
| 2,2,4,4,6,8,8-heptamethylnonane | Arlamol HD, isohexadecane | 13.0 |
| 1,2,3-propanetriol | glycerine | 5.0 |
| (2,5-dioxo-4-imidazolidinyl)urea | allantoin | 0.2 |
| 2,4-dihydroxy-N-(3-hydroxypropyl)-3,3-dimethylbutanamide | D-panthenol | 0.5 |
| 2-bromo-2-nitropropane-1,3-diol | Myacide BT | 0.03 |
| polyacrylic acid resin | Carbopol Ultrez 10, Carbomer | 0.45 |
| 2,6,10,15,19,23-hexamethyltetracosane | squalane | 1.0 |
| menthol | menthol | 0.1 |
| fragrance | perfume | 0.5 |
| tetrahydropropyl ethylenediamine | Neutrol TE (50%) | pH = 5.8 |
| demineralized water | water | balance |

The mixture is a milky-white emulsion.

Exemplary embodiment 2

FIG. 1 shows a plan view of a container 1 which serves as a reservoir for a shaving liquid according to the present invention. It is manufactured from a thin-walled plastic foil, e.g. polyethene, in the form of a flat flexible pouch having sealed rims 3. The plastic foil is coated with a thin impervious aluminum metal layer (not shown) in order to avoid sweating through of the shaving liquid. At one side of the pouch a hard plastic discharge spout 5 with a collar 7 is sealed between the rims. The spout contains an axial channel which opens into the reservoir formed by the pouch. When the discharge spout 5 is in action, it corresponds with a discharge opening in the shaving head of the electric shaver.

The shaving liquid according to the invention is a milky-white emulsion with excellent shaving characteristics, and does not attack or corrode plastic, metal and electrical parts, rubbers, printings and lacquers of the shaver. The combination of n-decyl glucoside and a liquid hydrocarbon, such as 2,2,4,4,6,8,8-heptamethylnonane, ensures that the shaving head and hair chamber can be very effectively rinsed with water, whereas said hydrocarbon provides excellent lubrication between the surface of the skin and the shaving head. Effective rinsing with water makes the shaver hygienic in use.

I claim:

1. A shaving liquid for a shaving system, which comprises water as a main component, additives and a surfactant, wherein the liquid is an emulsion of at least a liquid hydrocarbon in water, and the surfactant is n-decyl glucoside, said shaving liquid being water-rinseable and free of polysiloxanes.

2. A shaving liquid as claimed in claim 1, wherein the amount of n-decyl glucoside is 2 to 10% by weight.

3. A shaving liquid as claimed in claim 1, wherein the hydrocarbon is 2,2,4,4,6,8,8-heptamethylnonane in an amount of 10 to 25% by weight.

4. A shaving liquid as claimed in claim 1, wherein one of the additives is glycerine.

5. A container for an electric shaving system comprising a flexible reservoir and a discharge spout, wherein the reservoir is filled with a shaving liquid which comprises water as a main component, additives and a surfactant, wherein the liquid is an emulsion of at least a liquid hydrocarbon in water, the surfactant is n-decyl glucoside, the reservoir is a plastic pouch coated with a metal, said shaving liquid being water-rinseable from said electric shaving system and free of polysiloxanes.

* * * * *